United States Patent [19]

Hsia

[11] Patent Number: 4,857,636
[45] Date of Patent: Aug. 15, 1989

[54] PASTEURIZABLE, FREEZE-DRIABLE HEMOGLOBIN-BASED BLOOD SUBSTITUTE

[76] Inventor: Jen-Chang Hsia, 10 Cherry Hills Road, Concord, Ontario, Canada, M4K 2M4

[21] Appl. No.: 187,721

[22] Filed: Apr. 29, 1988

[30] Foreign Application Priority Data

May 5, 1987 [GB] United Kingdom ............... 8710598

[51] Int. Cl.$^4$ .................................. C07K 15/22
[52] U.S. Cl. ................................. 530/385; 514/6; 424/101
[58] Field of Search ................... 530/385; 514/6; 424/101

[56] References Cited

U.S. PATENT DOCUMENTS

| | | | |
|---|---|---|---|
| 3,925,344 | 12/1975 | Mazur | 530/385 |
| 4,001,200 | 1/1977 | Bonsen et al. | 530/385 |
| 4,061,736 | 12/1977 | Morris et al. | 530/385 |
| 4,336,248 | 6/1982 | Bonhard et al. | 530/385 |
| 4,473,496 | 9/1984 | Scannon | 530/385 |
| 4,529,719 | 7/1985 | Tye | 530/385 |
| 4,584,130 | 4/1986 | Bucci et al. | 530/385 |
| 4,600,531 | 7/1986 | Walder | 530/385 |

FOREIGN PATENT DOCUMENTS

PCTUS8400-
696   5/1984   PCT Int'l Appl. ............... 530/385

Primary Examiner—Howard E. Schain
Assistant Examiner—Susan M. Learned
Attorney, Agent, or Firm—Nixon & Vanderhye

[57] ABSTRACT

The present specification describes a process by which a blood substitute (hereinafter referred to as "Hemo-Safe") is derived from uniformly stabilized monomers and polymers of deoxyhemoglobin in its tight (T) conformation, with oxygen affinity similar to that of human blood. Two classes of HemoSafe are derived respectively from animal-hemoglobin and humanhemoglobin. HemoSafe (animal) differs from HemoSafe (human) in that it is free of polymers in order to reduce potential immunogenicity if used in man. Both types of Hemo-Safe may be derived in the following manner. The stabilized deoxyhemoglobins are converted to their carbon-monoxy derivatives (CO-HemoSafe) which are then stable under pasteurization conditions to render them viral disease transmission-free. CO-HemoSafes are stable for 2 months at 56° C. in either the solution or the freeze-dried state. For transfusion CO-HemoSafes are easily oxygenated under sterile conditions by photoconversion yielding oxy-HemoSafe. In addition a transfusable met-hemoglobin derivative for treatment of cyanide poisoning, is derived by converting oxy-HemoSafe to met-HemoSafe.

15 Claims, 3 Drawing Sheets

OXYGEN DISSOCIATION CURVE

FIG.3

FIG.4   HALFLIFE STUDY IN RAT

FIG.5

PASTEURIZABLE, FREEZE-DRIABLE HEMOGLOBIN-BASED BLOOD SUBSTITUTE

FIELD OF THE INVENTION

This invention relates generally to the stabilization of biomacromolecules in unique conformational states, and utilization of their associated activities and functions for biomedical and biotechnological applications. More specifically, hemoglobin (Hb), in either or its natural conformations [tight Hb(T) or relaxed Hb(R)], is stabilized and/or cross-linked to prevent dissociation and to achieve desired ligand-binding affinity. Processes and reagents are developed for the preparation of a family of new animal-hemoglobin, human-hemoglobin and genetically engineered hemoglobin-based substitutes for the oxygen delivery function of red blood cells, or "blood substitutes", and conversion of the oxyhemoglobin derivative to the met-hemoglobin derivatives for use in treating cyanide poisoning.

DESCRIPTION OF THE PRIOR ART

There are severe limitations on the use of blood as a transfusion fluid. These stem largely from the natural characteristics of red blood cells (RBC) and the danger of disease transmission.

Viral disease transmission by blood and blood products is a major problem in transfusion medicine. Screening to detect virally infected blood is costly and not completely effective. Of the available methods for inactivating viral infection in blood-derived pharmaceuticals, an industry standard is wet-heat pasteurization. RBC are not, however, pasteurizable.

Other limitations on the use of whole blood in transfusion include the rigorous storage requirements, short shelf-life, and complex immunologic characteristics of RBC. Hence, extensive research has been done to develop a cell-free, hemoglobin-based blood substitute through chemical modification of stroma-free hemoglobin.

As is well known, hemoglobin naturally comprises a tetramer of four subunits, made up of two alpha ($\alpha$) and two beta ($\beta$) globin chains. The molecular weight of the tetramer is about 64 kilo-daltons, and each of the subunits has approximately the same molecular weight. In dilute solution, tetrameric hemoglobin readily dissociates into half molecules of $\alpha\beta$ dimers. The relatively low molecular weight of these dimers is such that they are rapidly filtered from the circulation by the kidney and lost in the urine. This results in an unacceptably short half-life (T $\frac{1}{2}$) of approximately 2-3 hours.

Furthermore, hemoglobin without the protection of its red cell membrane loses its natural ligand diphosphoglycerate (DPG). DPG normally lowers the oxygen affinity of hemoglobin, so that, after it is lost, soluble hemoglobin binds oxygen more tightly and does not deliver oxygen to the tissue as efficiently as do red blood cells. For these reasons, stroma-free hemoglobin is not suitable for use as a blood substitute.

These defects have been addressed in the past by covalently attaching DPG analogues such as pyridoxal-5'-phosphate (PLP), to hemoglobin in its deoxy-state Hb(T), yielding PLP-Hb which has a lower oxygen affinity approaching that of RBC. Accordingly, Greenburg (Greenburg et al., Surgery, vol. 86 (1979), pp. 13-16) explored the use of PLP-Hb with physiological oxygen affinity as a blood substitute. However, without intramolecular crosslinking PLP-Hb, like SFH, dissociates into half-molecules and is rapidly excreted by the kidney. Furthermore, Hsia and coworkers (McGarrity et al., Journal of Chromatography, vol. 419 (1987), pp. 37-50) have shown that PLP-Hb is a complex mixture of modified hemoglobins containing between 0 and 6 moles of PLP per mole of hemoglobin, each of these subspecies having a different oxygen affinity.

DPG analogues have been shown to cross-link Hb intramolecularly. These cross-linkers are designed to bind specifically to the DPG-binding site of human hemoglobin. They include reagents specific for $\beta$ subunits (Benesch et al., Biochem. Biophys. Res. Commun., Vol. 63, No. 4 (1975), pp. 1123-1129; Benesch et al. in Methods in Enzymology, Vol. 76. Hemoglobins (1981) pp. 147-159 Academic Press) or $\alpha$ subunits (Chatterjee et al., Journal of Biol. Chem., Vol. 261, July 25, 1986, pp. 9929-9937).

Cross-linking by these specific ligands generally gives low yield (<70%) and requires further purification of products. Activated triphosphate nucleotides have been used simultaneously to cross-link hemoglobin and to occupy the DPG binding site, yielding ATP-Hb which was found to have lower oxygen affinity than PLP-Hb, and longer plasma retention time. (Greenburg et al., Progress in Clinical and Biological Research, Vol. 122, Advances in Blood Substitute Research (1983), pp. 9-17, Alan R. Liss, New York; McGarrity et al., Journal of Chromatography, Vol 415, (1987), pp. 136-142. At 80-90% blood replacement, ATP-Hb is extravasated into pleural and peritoneal spaces, so that it may not be safe to use at high levels of blood replacement.

Intermolecular cross-linking (polymerization) of PLP-Hb by a nonspecific cross-linker [e.g. glutaraldehyde (GA)] was introduced to prolong plasma retention time (Bonhard et al., U.S. Pat. No. 4,136,093, Jan. 23, 1979). The resulting polymric PLP-Hb (14 g Hb/dl) had physiological oxygen-carrying capacity (up to 20 cc $O_2$ per dl) and iso-oncotic pressure. However, the polymerization is incomplete and its components have heterogeneous oxygen affinity.

Yet other groups have attempted to prolong plasma half-life by conjugating PLP-Hb with polyethylene glycol (Iwasaki et al., Artificial Organs, Vol. 10, No. 5, (1986), pp. 411-416), inulin (Iwasaki et al., Biochem. Biophys. Res. Commun., Vol 113, No. 2 (1983), pp. 513-518), and Hb with dextran (Tam et al., Proc. Nat'l. Acad. Sci., USA, Vol. 73, (1976), pp. 2128-2131). The heterogeneity of the products and their high oxygen affinity were again drawbacks.

Polymerization of Hb using a variety of divalent cross-linkers yielding poly Hb as a blood substitute has been described in the prior art. The drawbacks of this approach are excess polymerization (90% of the product is greater than 150 kilodaltons in size), variable oxygen affinity, complex reaction schemes, and biological incompatibility of the cross-linkers used (e.g. divinyl sulfone, a potential carcinogen-U.S. Pat. Nos. 4,001,200; 4,001,401; 4,053,590). In a follow-up to this approach, the same family of divalent reagents has been used to produce intramolecularly cross-linked Hb. Again, divinyl sulfone has been shown to give a product with variable oxygen affinity and unspecified composition (U.S. Pat. No. 4,061,736).

It is an object of the invention to provide novel blood substitutes and processes for their preparation.

It is a further object of this invention to provide stabilized and pasteurized hemoglobin useful as a therapeutic agent in transfusion medicine, said pasteurization rendering the hemoglobin substantially free of transmissible infection agents.

A further object is to make available cross-linking agents and processes which cause hemoglobin to become intramolecularly cross-linked in either of its natural molecular conformations, (tight (T) or relaxed (R)), such that conformation is retained in the cross-linked product, which is then said to be conformationally stabilized. Such conformational stabilization is applicable to biomacromolecules in general.

SUMMARY OF THE INVENTION

The present invention is based upon a novel manner of stabilizing hemoglobin in its tetrameric form, which yields a hemoglobin tetramer not only stabilized against dissociation into dimers, or monomers, but is also stabilized in either of the natural conformations of Hb, namely tight (T) as normally assumed by deoxyhemoglobin, or relaxed (R) as normally assumed by oxyhemoglobin. Instead of using DPG analogues to stabilize and cross-link Hb(T), the products of the present invention are stabilized against both dissociation and conformational change by covalent chemical linkages between globin chains of the respective sub-units. Whatever the conformation of the starting tetrameric hemoglobin, T or R, that conformation is retained in the stabilized product according to the invention.

The ability of Hb to shift between conformations is reflected by the Hill coefficient (n). A coefficient of 2 or more indicates cooperative oxygen binding between subunits through conformational change, while a coefficient approximating to 1 indicates that Hb is locked in the T or R conformation. A Hill coefficient approximating to 1-1.5, indicating complete stabilization and the absence of co-operativity in oxygen binding, is a distinctive feature of the present invention.

A further distinction of the present invention over the prior art is that in the prior art, stabilization of hemoglobin is accomplished by linking globin chains of the sub-units at specific sites to make up the hemoglobin tetramer. These products are stabilized only against dissociation of the tetrameric units into dimeric sub-units, i.e. cooperative binding of oxygen is retained (Hill coefficient n~3). The present invention, in contrast, stabilizes tetrameric hemoglobin not only against dissociation but also against conformational change, i.e. no cooperative oxygen binding (Hill coefficient n~1-1.5). This feature of conformational stability is unique to the products of this invention.

The conformationally stabilized tetrameric hemoglobin of the present invention shows a number of significant advantages. For example, the very fact that it is stabilized into the T-conformation, and remains in that conformation in solution, confers on the product an oxygen affinity approximating that of natural red blood cells. The products of the invention are therefore substantially equivalent with red blood cells in respect of their oxygen uptake at the lungs. Another important feature is their ability to deliver oxygen to the body tissues. Under the oxygen partial pressure experienced in the body tissues, the T-conformational stabilized products of the invention will release a substantially greater quantity of oxygen to the tissues than allosterically cooperative, non-conformationally stabilized hemoglobin products. This high oxygen release to tissue becomes very important for example, when transfusing to the tissue-injured trauma patient, as commonly encountered in emergency medicine.

A very significant contrast of the present invention with the prior art is that the stabilized hemoglobin (HemoSafe I), according to the invention is readily produced in high yield, (at least 95%) in a single reaction step, substantially free from residual unstabilized hemoglobin. This does not require further purification, so that there is very little percent formation of low molecular weight dimeric product in solution, even without subsequent purification to remove residual unreacted material. Accordingly, the conformationally stabilized, Hb in the form of tetrameric units (hereinafter sometimes referred to as HemoSafe I) has a plasma half-life of about three times that of stroma-free hemoglobin and so may be well suited for use as a blood substitute in emergency situations. In addition, this stabilized tetrameric Hb(T) is eminently suited to the preparation of other novel hemoglobin-based products. Tetrameric Hb(T) can be linked together to form a polymerized hemoglobin, (poly Hb(T) or HemoSafe II) useful as a blood substitute and in most circumstances preferred as such to the stabilized tetrameric product on account of its increased molecular weight, conferring longer plasma half-life. The stabilized tetrameric Hb can be covalently linked to a second bio-polymer to form a conjugate (HemoSafe I-conjugate), useful as blood substitutes. In all of these conversions, the hemoglobin tetramers retain their specific conformation (e.g. Hb(T)). The product can be lyophilized for extended storage.

Moreover, and of great practical significance, it has been found that the conformationally stabilized heme-containing tetramers of the present invention can be treated to avoid oxidation of the iron from the ferrous to the ferric state, e.g. by presence of oxygen displacers such as carbon monoxide or nitric oxide, or oxygen scavengers such as sodium dithionite, and then pasteurized to destroy any contaminating viruses. The products of the invention are sufficiently stable to withstand the heating required, to 60° C. for ten hours at least, for pasteurization without denaturing of the protein or decomposition of the product. This process can be applied to pasteurize the tetrameric, e.g. CO-HemoSafe I, the polymerized, e.g. CO-HemoSafe II and the CO-HemoSafe I-conjugate. Then these CO HemoSafes can be readily reconverted to oxy-HemoSafes which are suitable for transfusion as blood substitutes, all without significant loss of their conformational functional and structural integrity.

Further, the products can be oxidized, without or without polymerization or conjugation, to met-hemoglobin products, (i.e. met-HemoSafes) effective as cyanide scavengers and usable for such purposes prophylactically.

Thus, according to the present invention, in a broad aspect, there is provided a hemoglobin product consisting essentially of tetrameric hemoglobin units stabilized against dissociation into dimers and stabilized against conformational change between the T-conformation and the R-conformation upon formation of aqueous preparations thereof, said tetrameric units having covalent chemical linkages between globin chains of the sub-units to effect the stabilization.

DETAILED DESCRIPTION OF THE INVENTION

In the preparation of products of the invention, novel reagents, reaction conditions and processes for stabilization of a uniform composition of deoxy-HB (Hb(T)), and for protecting it from instability under freezing or up to a temperature of 60° C., have been developed to achieve pasteurization, lyophilization and uniform physiological oxygen affinity of the finished products.

Conformation Specific Stabilizers and Cross-linkers (CSSC)

The preferred method of achieving the desired conformational and intramolecular stabilization of the tetrameric hemoglobin units according to the invention is by reaction with one or more of a class of reagents called conformation-specific stabilizers and cross-linkers (CSSC). Most commonly, these are dialdehydes or polyaldehydes. They react with primary amino groups on the globin chains, to form Schiff base linkages, which can subsequently be reduced to secondary amine linkages. In tetrameric hemoglobin, there are appropriately located primary amine groups on the $\alpha$-chains and the $\beta$-chains which will react preferentially and to all intents and purposes selectively with dialdehydes and polyaldehydes to form the desired covalent linkages for stabilization.

One example of a dialdehyde for use in the present invention as a CSSC is glutaraldehyde, (GA), when used under proper conditions. Reaction of hemoglobins with GA has been reported previously. These previous processes, however, have been conducted under conditions which did not lead to essentially complete stabilization of conformation of the tetrameric units, and did not lead to a product consisting essentially of stabilized tetramers. As previously used, glutaraldehyde is a non-specific reagent, and causes covalent intermolecular linking between tetramers to form polymerized hemoglobin faster than it forms intramolecular links between sub-units of a tetramer to stabilize it. The result is a mixture of stabilized tetramer, unstabilized tetramer, and stabilized polymer of wide molecular weight distribution, each component having different oxygen affinity.

In the present invention, hemoglobin is reacted with GA using a low concentration of hemoglobin (i.e., 1-g/dl) and a high molar ratio of GA to hemoglobin (i.e., from about 6:1 to about 60:1). Under these conditions, at least 95% and commonly at least 98% stabilization of the Hb monomers in tetrameric form is achieved in the polymerized hemoglobin. An essentially completely conformationally stabilized and polymerized product is thereby achieved. The stabilized polymeric form can then be carbon monoxylated for pasteurization.

If animal hemoglobin-based blood substitutes are to be used in man, formation of oligomers and polymers should be prevented because of their antigenicity.

During the process of fixing the Hb in the monomeric form, Hb(T), with GA, there is strong tendency towards polymerization. Therefore, a preferred embodiment of the invention employs different CSSC reagents and reaction conditions in the stabilization of hemoglobin (Hb). Use of these CSSC compounds can achieve stabilization of the Hb monomers, minimum dimer formation (<5%) with no detectable polymers, and, as well, the different CSSC compounds can generally be used to stabilize other macromolecules in the conformations chosen, with minimum polymerization, if desired. Such CSSC compounds, by stabilizing macromolecules in unique conformational states, permit the preservation of the activity and function of the bio macromolecule. However, use of CSSC compounds can additionally permit manipulation of the reaction conditions deliberately to link macromolecules to each other (polymerization), and alternatively to conjugate them to a different macromolecule, e.g. Inulin. Specifically, using deoxy hemoglobin in its tight (T) conformation (Hb(T)), with such a CSSC compound as the linking reagent, the reaction conditions can be manipulated to allow polymerization of the stabilized Hb(T) monomers, if desired, as well as linking of stabilized Hb(T) with different macromolecules. Such CSSC compounds can also be used to stabilize and to polymerize hemoglobin derivatives, e.g. PLP-Hb, depending on reaction conditions, and additionally, to link such derivatives to different macromolecules.

The CSSC compounds used in the present invention are generally dialdehydes or polyaldehydes. One specific example thereof is glyoxal, of the formula HOC-COH. Other specific examples are benzene dialdehydes (ortho, meta and para), although aromatic cross-linkers are less preferred because of the risk of immunogenic reaction from the residual aromatic groups. Most preferred as CSSC compounds are the aldehydic products produced by oxidative ring opening reactions on monosaccharides and oligosaccharides. Such reactions, e.g. using periodate oxidation, are known. The reaction yields a product having two aldehyde groups for each sugar monomer in the oligosaccharide. Thus, six aldehyde groups derive from a raffinose (o-raffinose) or maltotriose (o-maltotriose), for example. Without a homologous series, the number of molar equivalents of the polyaldehyde cross linkers, required to achieve the same extent of stabilization of the sub-units as a divalent aldehyde such as glucose, is inversely proportional to the valency of the CSSC. In contrast to GA, o-raffinose is intramolecular cross-linking specific, so that higher molar ratios of o-raffinose to Hb (20:1) can be used in the preparation of polymer-free Hb(T). This discovery demonstrates that CSSC effectively stabilizes Hb monomers into specific conformation with minimal intermolecular cross-linking. This affords more effective control of the reaction through slowing of the polymerization process, and allows easier production of an essentially polymer-free stabilized Hb product.

Specific examples of useful CSSC compounds include a homologous series of periodate oxidized saccharides of glucose, inulin, maltose, maltotriose, maltotetrose, maltopentose, maltohexose and maltoheptose. In general, the CSSC compounds derived from ring opening oxidation of sugars correspond to the formula where each of R, $R_1$, $R_2$, $R_3$, $R_4$ and $R_5$ is independently selected from hydrogen, hydroxyl, methoxy and hydroxymethyl; m is zero or one; and Q is a chemical group resulting from the oxidative ring opening of a di- or oligosaccharide having up to 36 sugar moieties.

When the starting compound is raffinose (a trisaccharide), the CSSC oxidation product has the formula:

When the starting compound is inulin, a polysaccharide, the CSSC oxidation product has the formula:

The cross-linking reagents used in the present invention are thus quite different from the DPG analogues conventionally used in the prior art to stabilize and cross-link Hb in its tetrameric form. They have no negatively charged groups such as phosphate, carboxylate or the like, and are not known specifically to react with the DPG of the Hb. Hence, they are able to effect the conformational stabilization of the Hb, of human and domestic animal origin, to retain each Hb unity in the conformation in which it encounters and reacts with the cross-linker. Water soluble cross-linkers are preferred for ease of reaction.

The relative amounts of aldehyde to hemoglobin are preferably arranged to provide a molar ratio of aldehyde groups to hemoglobin of at least 12:1, and preferably at least 60:1. Thus, when polyaldehydes are used, less polyaldehyde is required for the same amount of hemoglobin, than in the case of dialdehydes. The calculation of molar ratio is done on the assumption that hemoglobin has about 50 primary amine groups. Since the globin chain linking reactions in the present invention do not need to be site specific, excess molar ratio of aldehyde (e.g. for o-raffinose, molar ratio of 5–30 can be used preferably 20:1) can be used so as to obtain high yields (at least 95%) of stabilized product. Prior art processes requiring site specific reaction must use substantially stoichiometric amounts of reagents, with consequent decreases in yield. Reactions suitably take place in aqueous solution, at temperatures ranging from 4°–37° C. preferably at ambient temperatures. The pH of the reaction mixture should be controlled to between 6.7 and 9.5, preferably 8.0, by suitable buffering.

When using GA as the cross-linking reagent, to prepare poly Hb(T), a lower concentration of Hb in solution less than about 5–7 g/dl, should be used in order to exercise the necessary control over the reaction. With the other CSSC products, however, a greater range of Hb concentration can be used, e.g. from 1–20 g/dl, preferably 3–4 g/dl, since the reaction is more easily controllable.

Stroma free hemoglobin as obtained from red blood cells has a hemoglobin concentration of about 3–4 g/dl. It is most convenient to use this hemoglobin solution without dilution or concentration thereof. The preferred concentrations depend upon the choice of aldehyde. Thus, advantages of the novel CSSC over divalent GA are applicable equally to the production of polymer-free human Hb derivatives and of polymer-free animal Hb derivatives, but the prevention of poly Hb formation, using the novel CSSC such as o-raffinose, permits use of animal-Hb-derived HemoSafe products in man.

Stabilized Hemoglobin

In preparation of the conformationally stabilized and cross-linked deoxy-Hb (XL-Hb(T)) of the invention, the intramolecular cross-linking reaction can be terminated prior to the onset of the intermolecular cross-linking to form dimers, trimers, tetramers and high polymers, by addition of reducing or quenching agent at the appropriate time. The reaction of the primary amine groups with the aldehydic groups of the CSSC forms Schiff base linkages. Addition of sodium or potassium borohydride or the like reduces the Schiff base linkages to secondary amine linkages, and also reduces excess aldehydic groups to primary alcohols, thus arresting further cross-linking. The appropriate time for reduction can be ascertained through high pressure liquid chromatography (HPLC) analysis of a sample of the reaction mixture.

The conformationally stabilized tetrameric Hb product may be recovered and purified by standard techniques. Thus, it may be washed and concentrated by membrane filtration, and made up in physiological salt solution for use as a blood substitute, on an emergency basis where its relatively short half-life in the vascular system is acceptable. Alternatively, it may be used as the starting material for preparing other products according to the invention.

Polymerized stabilized hemoglobin

One of such other products is polymerized Hb (HemoSafe II), in which the conformationally stabilized and dissociatively stabilized tetrameric hemoglobin (HemoSafe I) is intermolecularly linked to form polymerized Hb, with a molecular weight preferably giving iso-oncotic pressure at a hemoglobin concentration of 14 g/dl. Polymerization is appropriately accomplished by use of dialdehydes or polyaldehydes, which may be the same as or different from those used for conferring conformational stability. Poly (Hb) products prepared in the prior art, for example, using glutaraldehyde have lacked the essentially complete conformational stability of the products of the present invention, since they have not been made from HemoSafe I.

Polymeric products according to the invention may contain a mixture of polymeric species, differing from one another in respect of their molecular weight (number of units in the polymer). However, all the species are conformationally stabilized in the T-conformation. All the species have the same or substantially the same oxygen affinity. Accordingly, the polymerized products of the invention have the advantages over the prior art of homogeneous oxygen affinity and readily reproducible composition.

Suitable conditions of reaction to produce the polymers are aqueous solution at room temperature, and in any event not exceeding about 37° C. The ratio of aldehyde to hemoglobin is suitably 2 to 100 on the basis of moles of aldehyde group per mole of Hb. The reaction solution should be buffered to within a pH of 6.7-9.5, preferably 8.0. The reaction can be terminated by addition of reducing agent such as sodium borohydride or sodium cyanoborohydride thereto, to reduce the residual aldehyde groups, and to convert the Schiff base to stable covalent carbon-nitrogen linkage.

A particularly preferred polymeric product composition of the invention has a molecular weight distribution in which from 20-25% of the constituent polymers consist of five or more tetrameric hemoglobin monomeric units, 50-60% of the constituent polymers have 2-4 hemoglobin monomeric units, 20-25% of the constituents are a single hemoglobin unit (molecular weight ~64 kilo dalton), and from 1-2% are incompletely stabilized hemoglobin. Such a composition is iso-oncotic at 14 g/dl, so that it can be used in equal volumes with blood as a blood substitute without causing blood pressure problems.

Stabilized-Hemoglobin conjugates

Another of such products is "conjugated HemoSafe I", in which the conformationally stabilized and dissociatively stabilized hemoglobin (HemoSafe I) is covalently conjugated to a bio-macromolecule to form a product of desirably high molecular weight. Conjugates of hemoglobin and bio-polymers (inulin, dextran, hydroxyethyl starch, etc.) are known in the prior art. In the present invention, however, whilst the same bio-polymers and similar methods of linking to hemoglobin can be adopted as in the prior art, the hemoglobin retains its conformational stability, preferably T, in the conjugate form, with the attendant advantages discussed above.

Particularly preferred as the polymer for preparing conjugates according to the present invention is inulin. This is a polysaccharide of approximately 5000 molecular weight, known for use in diagnostic aids.

Pasteurized Product

The prior art stabilization, polymerization, and conjugation processes described, do not protect the heme from oxidation, or the macromolecule from denaturation, when the macromolecule is subjected to heat, to drying or to freezing. It has now been discovered according to this invention, that the heme-containing macromolecule, when first stabilized, and optionally then polymerized or conjugated as described above, can be protected from thermal oxidation, e.g. by use of oxygen displacers or scavengers, or preferably by formation of heme-protecting complexes such as those formed by reaction with carbon monoxide (CO), or nitric oxide in such a manner as to form, for example, a carbon monoxy-heme derivative which permits pasteurization and freeze drying without denaturation.

Specifically, addition of CO to the novel, stabilized hemoglobins derived using GA, or using the CSSC products, yields novel products which are sometimes called herein CO-HemoSafe(s). For this purpose, CO may be added to the reaction mixture without isolation of the hemoglobin product therefrom. In the already stabilized hemoglobin, the protection of the heme by CO, and prevention of allosteric conformation changes together prevent oxidation and denaturation of CO-HemoSafe(s) under conditions of heat and freeze-drying. The carbon monoxylation and pasteurization as applied to HemoSafe I, HemoSafe II, and HemoSafe I-Inulin, or any other hemoglobin-based blood substitute, has not been described in the prior art.

Pasteurization (e.g. wet-heat at 60° C. for 10 hours) and lyophilization (freeze drying), of hemoglobin derivatives without addition of suitable protective agents leads to their precipitation and denaturation. By protecting the heme of the uniquely-stabilized hemoglobins of this invention with CO, heating and freeze drying of the product CO-HemoSafe can be successfully achieved. Successful pasteurization yields a soluble, undenatured CO-HemoSafe which is virus-disease transmission-free. Successful lyophilization then yields a dry CO-HemoSafe product. Both liquid and dry CO-HemoSafe products are stable to long term storage at any reasonable temperature, (e.g. 56° C. for 60 days). CO-HemoSafe is stable but does not deliver oxygen. Therefore, for use in transfusion, CO-HemoSafe solution is converted to oxy-HemoSafe solution by treatment with light in the presence of oxygen. Thus, another feature of this invention is the photoconversion of CO-HemoSafe to oxy-HemoSafe prior to transfusion.

The GA concentration (i.e. 5 mM) used in the initial stages of the present process is greater than that of 1 mM reported in the prior art to be necessary to inactivate 95% of the virus known as MTLV-III/LAV or HIV-I. However, assurance of viral transmission safety could be achieved by pasteurization, that is, heating to 60° C. for ten hours, which is the accepted standard treatment for plasma-derived pharmaceutical products like albumin. If, for example stabilized oxy-Hb(T), derived as above, were subjected to 60° C. for ten hours, a brown precipitate (i.e. denatured met-Hb(T)) would form, which is unsuitable for further use. Howevr, through conversion of stabilized Hb(T) to its carbon-monoxy derivative, CO-HemoSafe I(T) is formed which tolerates pasteurization and storage for up to 60 days in solution at 25° C. or 56° C., with no detectable change in physical-chemical properties such as its visible spectrum, oxygen affinity (i.e. $P_{50}$), or composition, as indicated by its HPLC profile. In addition, CO-HemoSafe I(T) can be freeze-dried and stored at 25° C. or 56° C. for 60 days without detectable changes in physical-chemical properties as described for pasteurization above.

Transfusible product

Pure CO-HemoSafe does not bind or transport oxygen, therefore it is unsuitable for oxygen delivery and transfusion despite its stability throughout the preparation, pasteurization and freeze drying procedures. Removal of CO under aseptic conditions is a prerequisite for its use as a blood substitute. The present invention, therefore, teaches that CO-HemoSafe can be readily photoconverted to the oxygenated derivative oxy-Hemoglobin. For this, oxygen may be supplied to the solution, and the solution may then be passed through a transparent tubing exposed to visible light. Optical absorption spectra of CO-HemoSafe and oxy-HemoSafe provide a convenient means of characterizing and quantitating the two species. In contrast to existing blood substitutes, like the currently available poly PLP-Hb, HemoSafe has the advantage of physiological and uniform oxygen affinity. Its precursor, CO-HemoSafe, displays stability under conditions of pasteurization, lyophilization, photoconversion and storage at any temperature up to 60° C. Thus, this invention teaches processes which produce a sterile viral-disease transmission-free and efficacious blood substitute.

In addition, in accordance with this invention, it has been found that the stability conferred by the process of carbon monoxylation can be applied to any Hb-based blood substitute described in prior art. For example, it has been demonstrated, according to the invention, that carbonmonoxy derivatives of poly PLP-Hb (poly CO-PLP-Hb), of ATP-Hb (CO-ATP-Hb), and of poly ATP-Hb (poly CO-ATP-Hb), are equally stable, pasteurizable, freeze dryable and photoconvertible to their oxy derivatives. Thus, the present invention includes processes applicable as a general requisite treatment to eradicate pathogenic viruses from oxygen carrying resuscitation fluids based on hemoglobin, and to improve their storage properties. Hence, all existing hemoglobin based blood substitutes such as dextran-Hb, hydroxyethyl starch Hb, polyethylene glycol-Hb, and diaspirin cross-linked Hb can be rendered virus-disease transmission free by the same processes described in the present application.

The preferred practical production process of HemoSafe of the present invention may be summarized as follows:

(i) Pooled whole blood is diluted with isotonic NaCl solution and applied to a membrane-type filtration system.
(ii) Plasma is separated from cellular elements of blood by tangential flow membrane filtration.
(iii) Red blood cells are washed in isotonic saline.
(iv) Red blood cells are lysed with hypotonic phosphate buffer. Then cell debris and other particulate matter are separated from soluble hemoglobin by tangential flow filtration.
(v) Oxy-Hb is converted to deoxy-Hb by vacuum or gas exchanging device and a reducing agent.
(vi) Deoxy-Hb is stabilized by the addition of a conformation specific stabilizing cross-linker (CSSC), in the monomer or polymer composition or conjugate as desired.
(vii) Deoxy-Hb is physically stabilized with carbon monoxide, yielding CO-HemoSafe.
(viii) CO-HemoSafe is washed and concentrated, or electrolyte balance is reestablished by addition of appropriate physiological salt solutions.
(ix) Pasteurization proceeds on the CO-HemoSafe.
(x) Pasteurized CO-HemoSafe is photoconverted, in the presence of oxygen, to oxy-HemoSafe.
(xi) Oxy-HemoSafe is sterile filtered and packaged for transfusion.

Once oxy-HemoSafe becomes available, as taught by this invention, it is possible to convert it to the met-hemoSafe derivative for use as an antidote and as a preventive transfusion in anticipation of cyanide poisoning such as in chemical defence. Thus, this invention teaches that after preparation of oxy-HemoSafe, known methods are used to oxidize it into met-HemoSafe, which can be transfused as an instantly effective and long acting cyanide scavenger. Using met-HemoSafe intravenously avoids the time delay attending of the body's utilization of oral nitrites to form met-Hb. Nitrites also necessarily recruit met-Hb from existing RBC oxyhemoglobin, thus use of met-HemoSafe does not compromise existing oxygen carrying capacity. Therefore, met-HemoSafe provides a treatment for cyanide intoxication beyond that used in prior art.

Transfusion of oxy-hemoSafe also can be used as a substitute for the blood doping technique. Whereas prior art teaches that red blood cells can be given to individuals to enhance their oxygen carrying capacity, the viscosity attending the red cells limits this increase to 10–15%. However, by using oxy-HemoSafe in conjunction with the known plasmapheresis technique, plasma can be replaced with oxy-HemoSafe, theoretically, increasing the oxygen carrying capacity by 50%, without changing the hematocrit or flow characteristics of the blood.

Whilst it is not intended that the invention or its scope should be limited to any particular theory of the structure of the products or mechanisms of the processes for their preparation, it is believed probable that the conformational stability and dissociative stability of the products may derive from intra-subunit, covalent linkages in the tetrameric hemoglobin by CSSC. These linkages are stable enough to prevent dissociation into dimers, and rigid enough to prevent conformational change. Whatever the structural explanation, the HemoSafes are unique in their conformational stability.

Moreover, the present invention is not limited in its scope to hemoglobin treatments and hemoglobin products. It is applicable to other proteins capable of existing in one or more conformations. Treatment of such proteins, whether in solution or in biological membranes with a CSSC compound according to the invention will stabilize the conformation in which the proteins encounter the CSSC. In theory, this should also stabilize biological activity associated with the stabilized conformation and render the molecule stable to pasteurization. Thus, it is of wide applicability to biological macromolecules including biologically active peptides, many of which are useful only in a particular conformation.

The invention is further described in the following specific, non-limiting examples, to which the various figures of drawings apply, as follows:

EXAMPLE 1

PREPARATION OF HUMAN AND ANIMAL STROMA-FREE HEMOGLOBIN

Human stroma-free hemoglobin was prepared from outdated blood or packed blood cells obtained from the Canadian Red Cross. First, the whole blood was centrifuged at 3,000 rpm for 30 minutes. Then, the plasma and buffy coat were removed by suction through a pipette and discarded. The sedimented erythrocytes were washed three time by suspending them in 3 times their volume of ice-cold normal saline. Following each wash, the cells were re-sedimented by centrifugation and the supernatant removed and discarded.

Next, the washed red cells were lysed with 4 volumes of 5 mM phosphate buffer, pH 7.6, to rupture the intact cell wall and free the hemoglobin. To remove stroma and membrane fragments, the hemolysate was filtered by a Pellicon Cassette System (Millipore) with a fluorocarbon polymer filter (HVLP, Porosity 0.5 μm), followed by a polysulphone filter (100,000 molecular weight cut-off). The hemoglobin in the filtrate was first concentrated to 14–20 g/dl and then washed with 10 volume excess of PBS buffer, pH 7.4, with a Pellicon Cassette System equipped with 5.0 sq. ft. of membrane cassette (PT series, 30,000 molecular weight cut off) and sterilized by filtration through a 0.22 μm Millipore filter unit and stored at 4° C. until use.

For animal hemoglobin preparations, the same procedure as that of human hemoglobin was used with the exception of rat hemoglobin where a 20 mM Borate buffer (pH 9.5) was substituted for the PBS buffer (pH 7.4) to enhance solubilization of the hemoglobin.

EXAMPLE 2

PREPARATION OF PERIODATE OXIDIZED RAFFINOSE AND OTHER SUGARS AS CSSC FOR HEMOGLOBIN 200 mg each of glucose, sucrose, raffinose, maltose, maltotriose, maltopentose, maltohexose, maltoheptose and other sugars in 6 ml of distilled $H_2O$ were treated with a fixed molar ratio of solid sodium m-periodate per saccharide at room temperature. (The molar ratio of sodium m-periodate per saccharide used was 2.2 for pyranoside and 1.1 for furanoside). After one hour, the reaction mixture was cooled in an ice-water bath, sodium bisulfite was added with vigorous stirring until the precipitated iodine was redissolved to yield a colorless solution. The pH of the solution was then immediately adjusted to 8.0±0.1 by the addition of 6N NaOH. The resulting oxidized sugar solutions were further diluted to give a final concentration of 20 mg/ml and filtered through a Millipore 0.45 μm type GS membrane filter and stored at 4° C. until use.

EXAMPLE 3

PREPARATION OF HUMAN HEMOSAFE I (T) CONFORMATIONALLY STABILIZED AND CROSS-LINKED BY RING-OPENED RAFFINOSE (O-RAFFINOSE)

Preparation of intramolecularly cross-linked deoxyhemoglobin (XL-Hb(T)): A 350 ml solution of stroma free oxyhemoglobin (Hb(R)) 1% W/V in 0.1M phosphate buffer, pH 8.0, under magnetic stirring was converted to deoxyhemoglobin (Hb(T)) under vacuum for approximately 4 hours at room temperature. 0.1 m mole of sodium dithionite dissolved in 0.3 ml of degassed buffer was added to the hemoglobin solution and allowed to react for 5 minutes. The cross-linking agent, o-raffinose, 1.08 m mole in 20 ml of previously degassed buffer, pH 8.0, was added under vacuum with vigorous stirring and the solution stirred for 4 hours at room temperature. The reaction mixture was cooled in an ice-water bath, and 15.0 m moles of sodium borohydride in 5 ml of degassed 1 mM NaOH under positive inert gas pressure was added. Reduction was allowed to proceed for 45 minutes.

Figure 1:
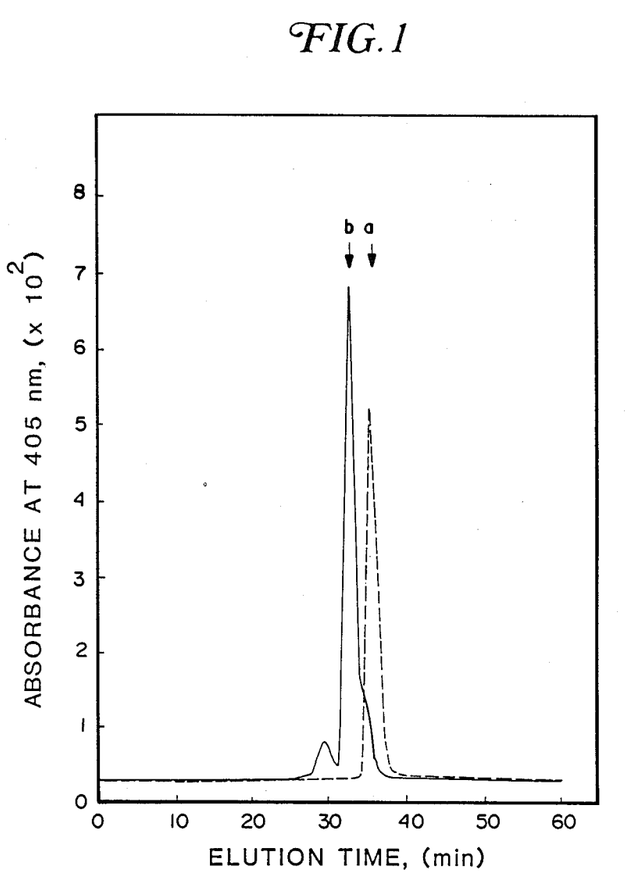
FIG. 1 is the analytical gel permeation High Pressure Liquid Chromatograph (HPLC) profile of the stabilized human deoxy hemoglobin produced according to Example 3 below, with a comparison to SFH.

FIG. 1 is the HPLC profile obtained from 5 μg/100 ml of the product (solid line), and a control human SFH (dashed line). Molecular weight calibrations indicative of B-globin half molecules (peak a) and $(\beta B)_2$ stabilized human Hb(T), (peak b) are as marked. The buffer used was 50 mM phosphate and 150 mM NaCl, pH 7.0. The chromatogram was obtained on a Pharmacia FPLC system equipped with GP.250 gradient programmer, P500 pump, a model 482 chart recorder and a single path UV monitor with 405 nm filter.

The profile shows that greater than 95% of the hemoglobin is stabilized and cross-linked and less than 5% of the XL-Hb(T) dissociate into half-molecules. Under the same experimental conditions, hemoglobin completely dissociates into half-molecules.

Preparation of the carbon monoxide (CO) derivative of XL-Hb(T) (COXL-Hb(T)) and pasteurization: Following the reduction with sodium borohydride, CO was bubbled directly into the XL-Hb(T) reaction mixture. After washing and concentration by membrane filtration, the COXLHb(T) under 100% CO was pasteurized at atmospheric pressure by heating for 10 hours at 60° C. to give CO-HemoSafe I. For long term storage at ambient temperature, CO-HemoSafe I can be lyophilized to a dry powder and reconstituted with a buffer when needed.

Photoconversion of CO-HemoSafe I(T) to oxy-HemoSafe I(T): 15 ml of CO-HemoSafe I(T) was transferred into a 500 ml round bottom flask which was attached onto a rotary evaporator and continuously rotated in an ice-water bath at 0° C. under a CGE Brooder Lamp. (C 250 R40/1, inside frost, soft glass) The flask was evacuated with an aspirator or a vacuum pump for the removal of unbound CO. After 2 minutes, air or 100% oxygen was introduced. This cycle was repeated until the composition of the sample checked spectrophotometrically between 577 and 560 mm gave an absorbency ratio of 1.8, after which removal of CO was considered complete (Methods in Enzymology, vol. 76, Hemoglobin, pp. 60 & 164). The final product so obtained has unaltered gel permeation chromatographic composition, shown in FIG. 1.

Figure 3:
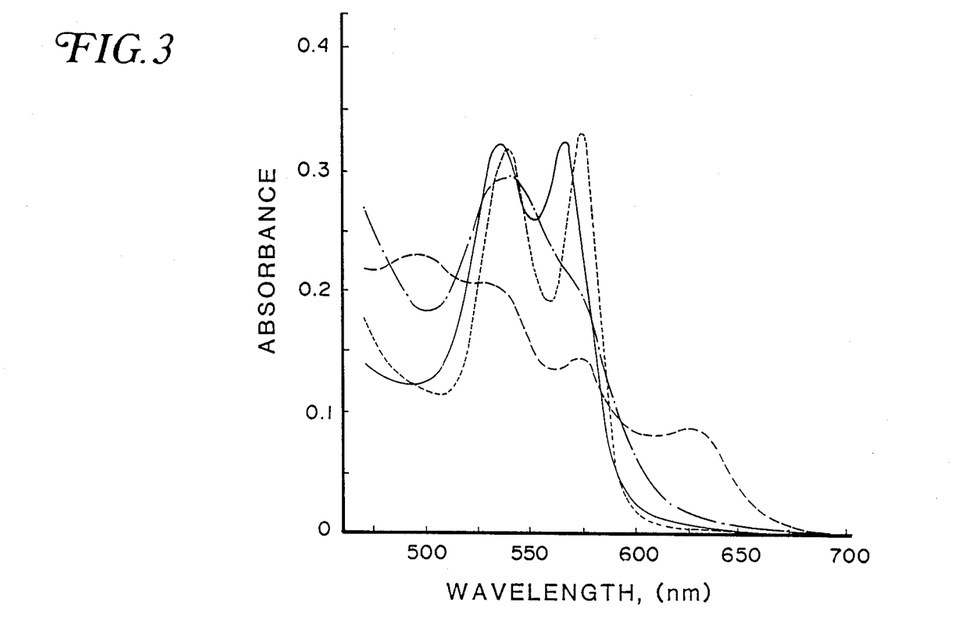
FIG. 3 shows absorption spectra of the products of Example 3 and Example 15.

FIG. 3 illustrates the relative absorption spectra of the products of this and other examples, in Ringer's buffer pH 7.4 at 22° C. The solid line is that of the XL-Hb(T), i.e. prior to carbon monoxylation, and the dotted line is that of the oxy-HemoSafe final product. These curves on FIG. 3 show that the final product has essentially unaltered physical-chemical properties.

Figure 2:
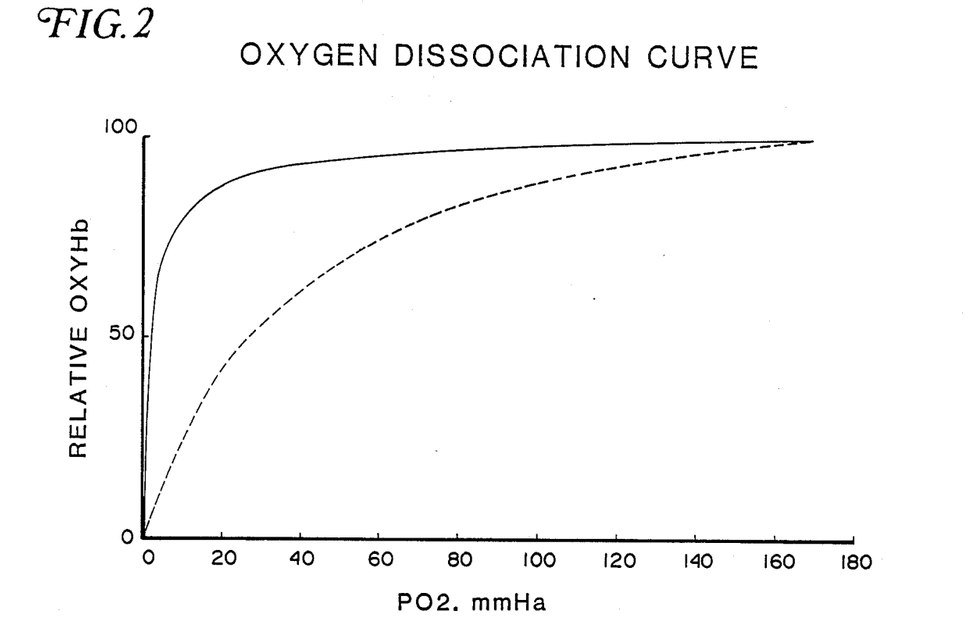
FIG. 2 is an oxygen dissociation curve of the HemoSafe (1) products of Examples 3 and 4.

FIG. 2 is the oxygen dissociation curve of the Hemo-Safe (1) cross-linked and stabilized by o-raffinose in this Example (dashed line) and that of oxy-hemoglobin or Hb(R) (solid line), measured at 37° C. in Ringer's phosphate buffer at pH 7.4 with hemoglobin concentration at 3.5 g/dl. These are typical curves of such products. Values of partial pressure of oxygen at 50% saturation ($P_{50}$) are read directly from the curve.

The HemoSafe (1) product of this Example shows according to FIG. 2 a hyperbolic oxygen dissociation curve with a $P_{50}$ value ($P_{50}$ is partial pressure of oxygen at which 50% of the hemoglobin is in the oxygenated state) of 27 mmHg at 37° C. in PBS buffer, (pH 7.4). It has a Hill coefficient of ~1–1.5.

Figure 4:
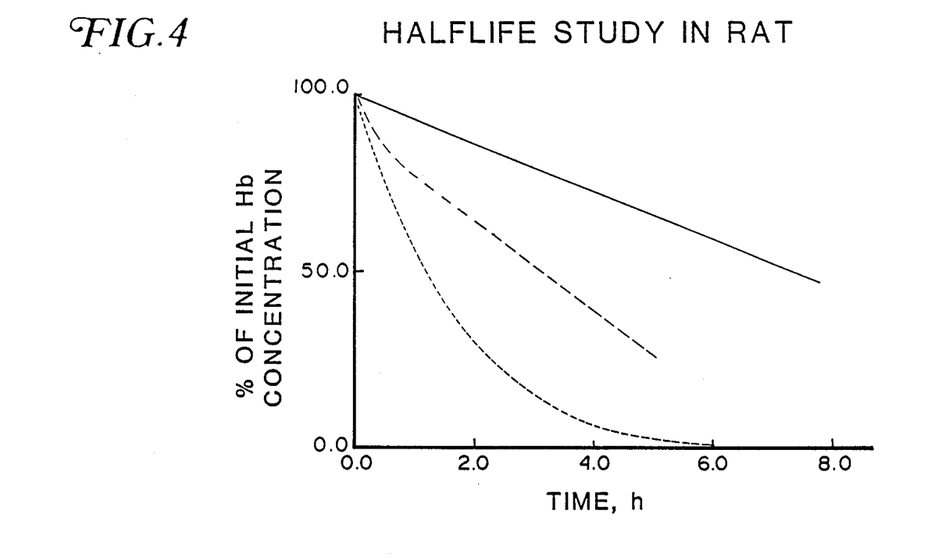
FIG. 4 is a graphical presentation of half-life studies of the products of Example 3, Example 9 and SFH.

On FIG. 4, there are presented typical plasma half-life studies of hemoglobin-based blood substitutes including, on the dashed line, that of the final oxy-HemoSafe I(T) product of this Example. The measurements are made in rats in a 30% hypervolemic model. The product has a half-life of approximately 4–5 hours as compared with that of hemoglobin (dotted line) of about 1–1.5 hours.

EXAMPLE 4

PREPARATION OF HUMAN HEMOSAFE I(R) CONFORMATIONALLY STABILIZED AND CROSS-LINKED BY RING-OPENED RAFFINOSE (O-RAFFINOSE)

The procedure is similar to that of HemoSafe I(T), described in Example 3, with the exception that the reaction was carried out under oxy state and in the absence of sodium dithionite.

The final product shows a hyperbolic oxygen dissociation curve with $P_{50}$ value of 2–3 mmHg at 37° C. in PBS buffer, pH 7.4, (FIG. 2, solid line) and its gel permeation chromatographic composition and visible spectrum are indistinguishable from those of HemoSafe I(T).

EXAMPLE 5

PREPARATION OF HUMAN HEMOSAFE I(T) CONFORMATIONALLY STABILIZED AND CROSS-LINKED BY GLYOXAL

Preparation of intramolecularly cross-linked stroma-free deoxyhemoglobin with glyoxal: Human stroma-free hemoglobin 2.9 g, 4% w/v in 0.1M sodium bicarbonate under magnetic stirring was converted to deoxyhemoglobin under vacuum for approximately 2 hours. The cross-linking agent, glyoxal, 2.58 m moles in 7.5 ml of degassed 0.1M sodium bicarbonate was added and the solution stirred for 2 hours at room temperature. The reaction mixture was cooled in an ice-water bath and 6 m moles of sodium borohydride in 3 ml of degassed 1 mM NaOH was added under positive inert gas pressure. Reduction was allowed to proceed for 45 minutes. The HPLC gel permeation profile is similar to that of FIG. 1 which shows that greater than 90% of the hemoglobin is intramolecularly stabilized.

The procedures for the preparation of glyoxal stabilized CO-HemoSafe I(T), its pasteurization, lyophilization and photoconversion back to oxy-HemoSafe I(T) are similar to those described in Example 3. The final product has a half-life of about 3.5 hours measured in the rat with a 30% hypervolemic replacement.

EXAMPLE 6

PREPARATION OF BOVINE HEMOSAFE I(T) CONFORMATIONALLY STABILIZED AND CROSS-LINKED BY RING-OPENED RAFFINOSE (O-RAFFINOSE)

Preparation of intramolecularly cross-linked bovine deoxyhemoglobin: A 90 ml solution of bovine stroma-free oxyhemoglobin, 1% w/v in 0.1M phosphate buffer pH 8.0 under magnetic stirring was converted to deoxyhemoglobin under vacuum for approximately 2 hours at room temperature. 400μ moles of sodium dithionite dissolved in 0.3 ml of degassed buffer was added to the hemoglobin solution and allowed to react for 5 minutes. The cross-linking agent, o-raffinose, 276μ moles in 6 ml of previously degassed buffer, pH 8.0 was added under vacuum and the solution stirred for 3 hours at room temperature. The reaction mixture was cooled in an ice-water bath, and 3.5 m moles of sodium borohydride in 2 ml of 1 mM NaOH (degassed) was added under positive inert gas pressure. Reduction was allowed to proceed for 45 minutes. The HPLC gel permeation chromatograpic profile shows that >90% of the bovine hemoglobin was intramolecularly stabilized. The chromatogram of cross-linked bovine hemoglobin is similar to that shown in FIG. 1.

The procedures for the preparation of o-raffinose stabilized bovine CO-HemoSafe I(T), its pasteurization, lyophilization and photoconversion to oxy-Hemosafe I(T) are similar to those desired in Example 3.

The final product so obtained has unaltered gel permeation chromatographic composition and physical-chemical properties. The product has a hyperbolic oxygen dissociation curve with $P_{50}$ of 34 mmHg measured at 37° C. in PBS buffer, pH 7.2, a Hill coefficient of ~1.5 and a plasma half-life of ~4 hours measured in 30% hypervolemic transfusion in rat.

EXAMPLE 7

PREPARATION OF OVINE HEMOSAFE I(T) CONFORMATIONALLY STABILIZED AND CROSS-LINKED BY RING-OPENED RAFFINOSE (O-RAFFINOSE)

Preparation of intramolecular cross-linked ovine deoxyhemoglobin: A 100 ml solution of sheep stroma-free oxyhemoglobin, 1% w/v in 0.1M phosphate buffer, pH 8.0, under magnetic stirring was converted to deoxyhemoglobin under vacuum for approximately 2 hours at room temperature. 50μ moles of sodium dithionite in 100 μl of degassed buffer was added to the hemoglobin solution. After 5 minutes, the cross-linking agent, o-raffinose, 616μ moles in 12.5 ml of previously degassed buffer pH 8.0 was added under vacuum with stirring. Cross-linking was allowed to proceed for 16 hours at 4° C. The reaction mixture was cooled in an ice-water bath, and 4.4 m moles of sodium borohydride in 2.5 ml of degassed 1 mM NaOH was added under positive inert gas pressure. Reduction was allowed to proceed for 45 minutes. The HPLC gel permeation chromatographic profile revealed that greater than 95% of the ovine hemoglobin half-molecule was intramolecularly stabilized, similar to that shown in FIG. 1.

The procedures for the preparation of o-raffinose stabilized ovine CO-HemoSafe I(T), its pasteurization, lyophilization and photoconversion back to oxy-HemoSafe I(T) are similar to those described in Example 3.

The final product so obtained has unaltered gel permeation chromatographic composition and physical-chemical properties. The product has a $P_{50}$ of 38 mmHg measured at 37° C. in PBS buffer, pH 7.4.

EXAMPLE 8

PREPARATION OF RAT HEMOSAFE I(T) CONFORMATIONALLY STABILIZED AND CROSS-LINKED BY RING-OPENED RAFFINOSE (O-RAFFINOSE)

Preparation of intramolecular cross-linked rat deoxyhemoglobin: A 18 ml solution of rat stroma-free oxy hemoglobin, 2% w/v in 20 mM Borate buffer, pH 9.5, under magnetic stirring was converted to deoxyhemoglobin under vacuum for approximately 1 hour at room temperature. 50μ moles of sodium dithionite dissolved in 0.1 ml of degassed buffer was added to the hemoglobin solution and allowed to react for 5 minutes. The cross-linking agent, o-raffinose, 110μ moles in 3 ml of previously degassed buffer, pH 8.0, was added under vacuum with stirring. Cross-linking was allowed to proceed for 16 hours at 4° C. The reaction mixture was cooled in an ice-water bath and 1.2 m moles of sodium borohydride in 1 ml of 1 mM NaOH was added under positive inert gas pressure. Reduction was allowed to proceed for 45 minutes. The HPLC gel permeation chromatographic profile shows that greater than 90% of the rat hemoglobin half-molecule was intramolecularly stabilized similar to that shown in FIG. 1.

The procedures for the preparation of o-raffinose stabilized rate CO-HemoSafe I(T), its pasteurization, lyophilization, and photoconversion back to oxy-HemoSafe I(T) are similar to those described in Example 3.

The final product obtained has unaltered gel permeation chromatographic composition and physical-chemical properties. The product has a $P_{50}$ of 24 mmHg measured at 37° C. in PBS buffer, pH 7.4, and a Hill coefficient of $\sim 1.0$.

EXAMPLE 9

PREPARATION OF HUMAN HEMOSAFE II CONFORMATIONALLY STABILIZED AND POLYMERIZED BY RING-OPENED RAFFINOSE (O-RAFFINOSE)

Preparation of intramolecularly stabilized and intermolecularly cross-linked human deoxyhemoglobin: A 77 ml solution of human oxyhemoglobin, 4% w/v in 0.1M phosphate buffer, pH 8.0, under magnetic stirring was converted to deoxyhemoglobin under vacuum for approximately 4 hours at room temperature. 0.10 m moles of sodium dithionite dissolved in 0.3 ml of degassed buffer was added to the hemoglobin solution and allowed to react for 5 minutes. The cross-linking agent, o-raffinose, 0.95 m moles in 20 ml of previously degassed buffer was added under vacuum and the reaction allowed to proceed for 6 hours. The reaction mixture was cooled in an ice-water bath, and 9.5 m moles of sodium borohydride in 4 ml of degassed 1 mM NaOH was added under positive inert gas pressure. Reduction was allowed to proceed for 45 minutes. In accompanying FIG. 5, the HPLC gel permeation chromatographic profile revealed that greater than 98% of the hemoglobin was stabilized and cross-linked with 20–25% being the stabilized monomer, 55 5% being the dimers, trimers and tetramers combined and 20–25% being the pentamers and higher polymers combined.

Figure 5:
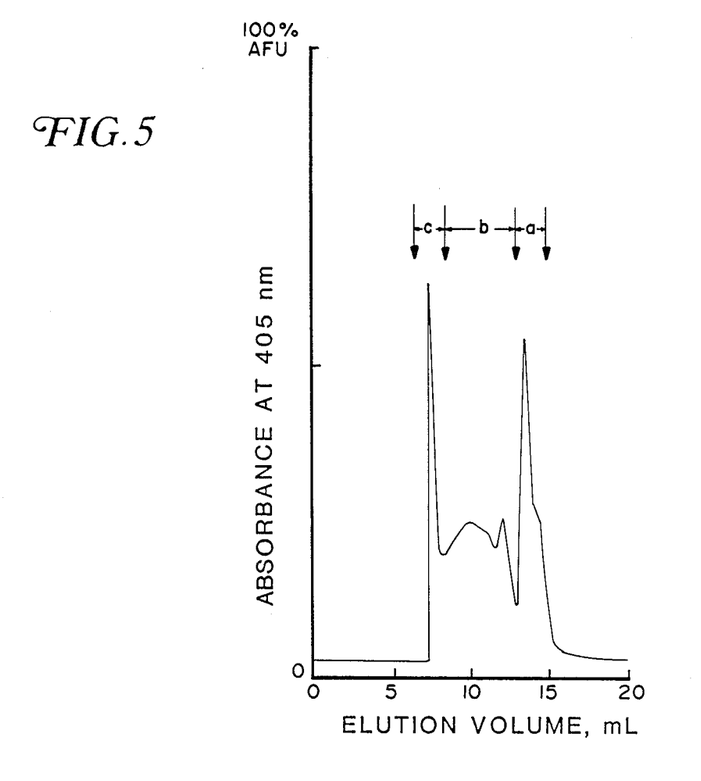
FIG. 5 is the analytical gel permeation High Pressure Liquid Chromatography (HPLC) profile of products according to the procedure of Example 9.

This chromatographic profile was obtained using as buffer 50 mM phosphate and 150 mM NaCl, pH 7, with the apparatus described for FIG. 1. The poly Hb(T) was resolved into monomers (peak a), the sum of dimer, trimer and tetramer (peak b) as well as pentamers or greater (peak c), on a Superose-12 prepacked HR 10/30 column at a flow-rate of 0.4 ml/min. Such a composition of the polymerized product was shown to be isooncotic at a concentration of 14 g/dl.

The procedures for the preparation of o-raffinose stabilized CO-HemoSafe II(T), its pasteurization, lyophilization and photoconversion back to oxyHemoSafe II(T) are similar to those described in Example 3.

The final product so obtained has unaltered gel permeation chromatographic composition and physical-chemical properties before and after pasteurization, has a hyperbolic oxygen dissociation curve with uniform $P_{50}$ of 32 mmHg, and a Hill coefficient 1.6 measured at 37° C. in PBS buffer, pH 7.2. The isolated purified fractions of HemoSafe II(T), i.e., monomer, dimer, trimer, tetramer, pentamer or greater (see FIG. 5) has indistinguishable $P_{50}$, a Hill coefficient and a half-life of 7–8 hours measured in rat with a 30% hypervolemic replacement.

EXAMPLE 10

PREPARATION OF HUMAN HEMOSAFE II CONFORMATIONALLY STABILIZED AND POLYMERIZED BY RING-OPENED SUCROSE (O-SUCROSE)

Preparation of intramolecular stabilized and intermolecular cross-linked human deoxyhemoglobin by o-sucrose: A 10 ml solution of human stroma-free oxyhemoglobin, 13% w/v in 0.1M phosphate buffer, pH 8.0, under magnetic stirring was converted to deoxyhemoglobin under vacuum for approximately 2 hours. 40$\mu$ moles of sodium dithionite dissolved in 0.2 ml of degassed buffer was added to the hemoglobin solution. After 5 minutes, the cross-linking agent, o-sucrose, 200$\mu$ moles in 3 ml of previously degassed buffer was added under vacuum and the reaction allowed to proceed for 6 hours. The reaction mixture was cooled in an ice-water bath, and 2.0 m moles of sodium borohydride in 1 ml of degassed 1 mM NaOH was added under positive inert gas pressure. Reduction was allowed to proceed for 45 minutes. The HPLC gel permeation chromatographic profile revealed that >98% of the hemoglobin was stabilized and cross-linked and the product composition is similar to that described in Example 9. (FIG. 5)

The procedures for the preparation of o-sucrose stabilized CO-HemoSafe II(T), its pasteurization, lyophilization and photoconversion back to oxyHemoSafe II(T) are similar to those described in Example 3.

The final product so obtained has unaltered gel permeation chromatographic composition and physical-chemical properties before and after pasteurization. The product has a $P_{50}$ of 24 mmHg measured at 37° C. in PBS buffer, pH 7.2, a Hill coefficient of 1.3 and a half-life of $\sim 7$–8 hours in rat, measured at 30% hypervolemic replacement.

EXAMPLE 11

PREPARATION OF HUMAN HEMOSAFE II(T) CONFORMATIONALLY STABILIZED AND POLYMERIZED BY GLUTARALDEHYDE

Preparation of intramolecular stabilized and intermolecular cross-linked human deoxyhemoglobin by glutaraldehyde: A 78 ml solution of human stroma-free oxyhemoglobin, 4% w/v in 0.1M phosphate buffer, pH 8.0, under magnetic stirring was converted to deoxyhemoglobin under vacuum for approximately 4 hours at room temperature. 0.1 m moles of sodium dithionite dissolved in 0.3 ml of degassed buffer was added to the hemoglobin solution and allowed to react for 5 minutes. The cross-linking agent, glutaraldehyde, 480$\mu$ moles in 2.5 ml of previously degassed buffer was added under vacuum and the reaction allow to proceed for 6 hours. The reaction mixture was cooled in an ice-water bath and 4 m moles of sodium borohydride in 4 ml of degassed 1 mM NaOH was added under positive inert gas pressure. Reduction was allowed to proceed for 45 minutes. The HPLC gel permeation chromatographic profile shows that >98% of the human hemoglobin was stabilized and cross-linked and the product composition is similar to that described in Example 9.

The procedures for the preparation of glutaraldehyde stabilized CO-HemoSafe II(T), its pasteurization, lyophilization and photoconversion back to oxy-HemoSafe II(T) are similar to those described in Example 3.

The final product so obtained has unaltered gel permeation chromatographic composition and physical properties. The product has a $P_{50}$ of ~30 mmHg measured at 37° C. in PBS buffer pH 7.4 and a Hill coefficient of 1.5 and a half-life of 7–8 hours, measured in rat with 30% hypervolemic replacement.

EXAMPLE 12

PREPARATION OF BOVINE HEMOSAFE II(T) CONFORMATIONALLY STABILIZED AND POLYMERIZED BY RING-OPENED RAFFINOSE (O-RAFFINOSE)

Preparation of intramolecular stabilized and intermolecular cross-linked bovine deoxyhemoglobin by o-raffinose: 40 ml solution of bovine stoma-free oxyhemoglobin, 6% w/v in 0.1M phosphate buffer, pH 8.0, under magnetic stirring was converted to deoxyhemoglobin under vacuum for approximately 4 hours at room temperature. 80$\mu$ moles of sodium dithionite dissolved in 0.2 ml of degassed buffer was added to the hemoglobin solution and was allowed to react for 5 minutes. The cross-linking agent, o-raffinose, 550$\mu$ moles in 10 ml of previously degassed buffer was added under vacuum and the reaction allowed to proceed for 6 hours. The reaction mixture was cooled in an ice-water bath and 3.5 m moles of sodium borohydride in 4.0 ml of degassed 1 mM NaOH was added under positive inert gas pressure. Reduction was allowed to proceed for 45 minutes. The HPLC gel permeation chromatographic profile shows that >95% of the bovine hemoglobin half-molecule was stabilized and cross-linked and the product composition is similar to that described in Example 9.

The procedures for the preparation of o-raffinose stabilized bovine CO-HemoSafe II(T), its pasteurization, lyophilization and photoconversion back to oxy-HemoSafe II(T) are similar to those described in Example 3.

The final product so obtained has unaltered gel permeation chromatographic composition and physical properties before and after pasteurization. The product has a $P_{50}$ of 28 mmHg measured at 37° C. in PBS buffer, pH 7.4, and a Hill coefficient of ~1.5 and a half-life of 7–8 hours measured in rat with a 30% hypervolemic replacement.

EXAMPLE 13

PREPARATION OF RAT HEMOSAFE II(T) CONFORMATIONALLY STABILIZED AND POLYMERIZED BY RING-OPENED RAFFINOSE (O-RAFFINOSE)

Preparation of intramolecular stabilized and intermolecular cross-linked rat deoxyhemoglobin: A 6 ml solution of rat stroma-free oxyhemoglobin, 9.4% w/v in 20 mM Borate buffer pH 9.5 under magnetic stirring was converted to deoxyhemoglobin under vacuum for approximately 2 hours at room temperature. 20$\mu$ moles of sodium dithionite dissolved in 100 $\mu$l of degassed buffer was added to the hemoglobin solution and allowed to react for 5 minutes. The cross-linking agent, o-raffinose, 87$\mu$ moles in 2 ml of previously degassed buffer was added under vacuum and the reaction allowed to proceed for 16 hours at 4° C., then 5 hours at room temperature. The reaction mixture was cooled in ice-water bath and 1.2 m moles of sodium borohydride in 1.0 ml of degassed 1 mM NaOH was added under positive inert gas pressure. Reduction was allowed to proceed for 45 minutes. The HPLC gel permeation chromatographic profile shows that >98% of the rat hemoglobin half-molecule was stabilized and cross-linked and the product composition is similar to that described in Example 9.

The procedures for the preparation of o-raffinose stabilized rat CO-HemoSafe II(T), its pasteurization, lyophilization and photoconversion back to oxy-HemoSafe II(T) are similar to those described in Example 3.

The final product so obtained has unaltered gel permeation chromatographic composition and physical-chemical properties before and after pasteurization.

EXAMPLE 14

PREPARATION OF RING-OPENED RAFFINOSE CONFORMATIONALLY STABILIZED HUMAN HEMOSAFE I(T)-INULIN CONJUGATE

Preparation of intramolecularly cross-linked human HemoSafe I(T). The preparation is identical to that described in Example 3.

Preparation of periodate oxidized Inulin (o-Inulin): The preparation of ring-opened inulin is similar to that described in Example 2.

Preparation of HemoSafe I(T)-Inulin conjugate: A 35 ml solution of human oxy-HemoSafe I(T)-Inulin conjugate: A 35 ml solution of human oxy-HemoSafe I(T) 4% w/v in 0.1M NaHCO$_3$ under magnetic stirring was converted to deoxyHemoSafe I(T) under vacuum for approximately 2 hours at room temperature. 40 moles of sodium dithionite dissolved in 50 $\mu$l of degassed buffer was added. After 5 minutes, equimolar of o-Inulin in 8.5 ml of previously degassed 0.1M NaHCO$_3$ was added under vacuum with stirring and the reaction allowed to proceed for 5 hours at room temperature. The reaction mixture was cooled in an ice-water bath, and 2.0 m moles of sodium borohydride in 1.5 ml of degassed 1 mM NaOH was added under positive inert gas pressure. Reduction was allowed to proceed for 45 minutes. The HPLC gel permeation chromatographic profile and product composition of HemoSafe I(T)-Inulin conjugate is similar to that shown in FIG. 5. The procedures for the preparation of raffinose stabilized human CO-HemoSafe I(T)-Inulin conjugate, its pasteurization, lyophilization, and photoconversion back to human oxy-HemoSafe I(T)-Inulin conjugate are similar to those described in Example 3.

The final product so obtained has unaltered gel permeation chromatographic composition and physical-chemical properties. The product has a $P_{50}$ of 27 mm Hg at 37° C. in PBS buffer, pH 7.2, a Hill coefficient of ~1.2, and a half-life of 7–8 hours measured in rat with a 30% hypervolemic replacement.

EXAMPLE 15

PREPARATION OF O-RAFFINOSE CONFORMATIONALLY STABILIZED HUMAN MET-HEMOSAFES I(T) AND (R)

After photoconversion of the CO-HemoSafes I(T) and (R) to their respective oxy-HemoSafes as described above, (Examples 3), the oxyHemoSafes were left at 37° C. to allow their conversion to met-HemoSafes. The conversion is considered complete after methemoglobin levels are >90% as characterized by the optical absorption spectra, presented as the dashed line on FIG. 3. Its efficacy as a CN scavenger is ascertained by its ability to yield the corresponding cyanomet-hemoglobin optical absorption spectrum, presented as the dashed-dotted line on FIG. 3.

EXAMPLE 16

PREPARATION OF O-RAFFINOSE CONFORMATIONALLY STABILIZED AND POLYMERIZED HUMAN MET-HEMOSAFE II(T) AND (R)

O-raffinose conformationally stabilized and polymerized human HemoSafe II(T) and (R) were prepared according to Example 9. These were converted to their respective met-HemoSafes as described in Example 15.

EXAMPLE 17

PREPARATION OF O-RAFFINOSE CONFORMATIONALLY STABILIZED HUMAN MET-HEMOSAFE I(T)-INULIN CONJUGATE

O-raffinose conformationally stabilized human HemoSafe I(T)-inulin conjugate was prepared according to Example 14 and converted to the met-HemoSafe as described in Example 15.

EXAMPLE 18

VIRAL INACTIVATION OF RAFFINOSE CONFORMATIONALLY STABILIZED AND POLYMERIZED HUMAN HEMOSAFE II

Human HemoSafe II was prepared according to Example 9. Samples were prepared consisting of HemoSafe II, HemoSafe II spiked with $10^4$ HIV units, and $10^4$ HIV units only. In control experiments, it was demonstrated that the presence of HemoSafe II in solution does not affect the infectivity of HIV-I. These samples were subjected to wet-heat at 56° C. for one week. At the end of this treatment, the samples were assayed for HIV infectivity using an antigen assay. No HIV infectivity was detected in any of the samples.

I claim:

1. A stabilized hemoglobin product consisting essentially of tetrameric hemoglobin units stabilized against dissociation into dimers, and stabilized against conformational change between the T-conformation and the R-conformation upon formation of aqueous preparations thereof, said tetrameric units having covalent chemical linkages between globin chains of the subunits to effect the stabilization, the covalent linkages being secondary amino linkages, formed by reaction of the hemoglobin with an aldehyde produced by oxidative ring opening of an oligosaccharide having at least two sugar moieties, followed by reduction of the so-formed Schiff base linkages to secondary amino linkages.

2. Stabilized hemoglobin product according to claim 1 which is conformationally stabilized into the T-conformation.

3. Stabilized hemoglobin product according to claim 1 wherein the oligosaccharide has up to 7 sugar moieties per molecule.

4. Stabilized hemoglobin product according to claim 3 wherein the oligosaccharide is raffinose.

5. Stabilized hemoglobin product according to claim 1 wherein the hemoglobin is of human origin.

6. Stabilized hemoglobin product according to claim 1 wherein the hemoglobin is of animal origin.

7. A stabilized hemoglobin product comprising a plurality of said stabilized tetrameric hemoglobin units according to claim 1, covalently linked together to form a polymeric hemoglobin product in which each hemoglobin unit has conformational stability and dissociative stability.

8. A stabilized polymeric hemoglobin product according to claim 7, wherein each hemoglobin unit thereof is stabilized in the T-conformation.

9. A stabilized polymeric hemoglobin product according to claim 8 and having a composition such that from 20–25% of the constituents are hemoglobin tetrameric units, 50–60% of the constituents are hemoglobin oligomers of 2–4 tetrameric hemoglobin units, 20–25% of the constituents are single hemoglobin tetramers, and 1–2% are dimers of hemoglobin subunits.

10. A stabilized hemoglobin product consisting essentially of tetrameric hemoglobin units stabilized against dissociation into dimers, and stabilized against conformational change between the T-conformation and the R-conformation upon formation of aqueous preparations thereof, said tetrameric units having covalent chemical linkages between globin chains of the subunits to effect the stabilization, the stabilized hemoglobin product being the reaction product of hemoglobin with an aldehyde derived from oxidative ring opening of an oligosaccharide having at least two sugar moieties.

11. The stabilized hemoglobin product of claim 10, which is conformationally stabilized into the T-conformation.

12. The stabilized hemoglobin product of claim 11, wherein the oligosaccharide has up to 7 sugar moieties per molecule.

13. The stabilized hemoglobin product of claim 12, wherein the oligosaccharide is raffinose.

14. The stabilized hemoglobin product of claim 10, wherein the hemoglobin is of human origin.

15. The stabilized hemoglobin product of claim 10 wherein the hemoglobin is of animal origin.

* * * * *